United States Patent
Tiberg et al.

(10) Patent No.: US 12,029,813 B2
(45) Date of Patent: Jul. 9, 2024

(54) INJECTABLE BUPRENORPHINE FORMULATION

(71) Applicant: CAMURUS AB, Lund (SE)

(72) Inventors: Fredrik Tiberg, Lund (SE); Markus Johnsson, Lund (SE); Ian Harwigsson, Lund (SE)

(73) Assignee: CAMURUS AB, Lund (SE)

( * ) Notice: Subject to any disclaimer, the term of this patent is extended or adjusted under 35 U.S.C. 154(b) by 236 days.

(21) Appl. No.: 17/234,989

(22) Filed: Apr. 20, 2021

(65) Prior Publication Data
US 2021/0308041 A1 Oct. 7, 2021

Related U.S. Application Data

(62) Division of application No. 15/520,946, filed as application No. PCT/EP2015/074901 on Oct. 27, 2015, now abandoned.

(30) Foreign Application Priority Data

Oct. 27, 2014 (GB) .................................. 1419091

(51) Int. Cl.
| | | |
|---|---|---|
| *A61K 9/00* | (2006.01) | |
| *A61K 31/485* | (2006.01) | |
| *A61K 47/12* | (2006.01) | |
| *A61K 47/20* | (2006.01) | |
| *A61K 47/22* | (2006.01) | |
| *A61K 47/44* | (2017.01) | |

(52) U.S. Cl.
CPC .......... *A61K 9/0019* (2013.01); *A61K 9/0024* (2013.01); *A61K 31/485* (2013.01); *A61K 47/12* (2013.01); *A61K 47/20* (2013.01); *A61K 47/22* (2013.01); *A61K 47/44* (2013.01)

(58) Field of Classification Search
CPC ...... A61K 31/485; A61K 47/12; A61K 47/20; A61K 47/22; A61K 47/44; A61K 9/0019; A61K 9/0024; A61K 47/14; A61K 9/0002; A61K 9/08; A61P 25/04; A61P 25/36; A61P 29/00
See application file for complete search history.

(56) References Cited

U.S. PATENT DOCUMENTS

| | | |
|---|---|---|
| 2005/0075361 A1 | 4/2005 | Wang |
| 2013/0190341 A1 | 7/2013 | Tiberg et al. |
| 2015/0359891 A1 | 12/2015 | Chen et al. |

FOREIGN PATENT DOCUMENTS

| | | | |
|---|---|---|---|
| CN | 103142458 A | | 6/2013 |
| EP | 1422230 A1 | | 5/2004 |
| GB | 2469792 A | | 11/2010 |
| WO | 2005/117830 A1 | | 12/2005 |
| WO | 2010/009451 A2 | | 1/2010 |
| WO | 2011/154724 A2 | | 12/2011 |
| WO | WO 2014/016428 | * | 1/2014 |

OTHER PUBLICATIONS

Sesame Oil (Sesame Oil (drugfuture.com), obtained from the internet with a date of Jul. 20, 2010, SP32-NF27 p. 1335, Pharmacopeial Forum: vol. No. 30(5) p. 1668).*
International Search Report and Written Opinion in International Application No. PCT/EP2015/074901, dated Jan. 1, 2016.
Zhang Guangjie "Application Technology of Pharmaceutical Excipients", pp. 23-24, China Medicine Industry Press, Dec. 1991.

* cited by examiner

*Primary Examiner* — James D. Anderson
(74) *Attorney, Agent, or Firm* — RAPHAEL BELLUM PLLC

(57) ABSTRACT

The present invention provides an injectable liquid formulation comprising: a) a lipid controlled-release matrix comprising at least 50% triacyl lipids; b) at least one oxygen containing organic solvent; c) at least 16% by weight of at least one active agent selected from buprenorphine and salts thereof, calculated as buprenorphine free base. The invention also provides a method for the treatment of pain, for opioid maintenance therapy or for the treatment of opioid dependence by detoxification and/or maintenance or for the treatment or prophylaxis of the symptoms of opioid withdrawal and/or cocaine withdrawal by injecting such a liquid composition.

22 Claims, 1 Drawing Sheet

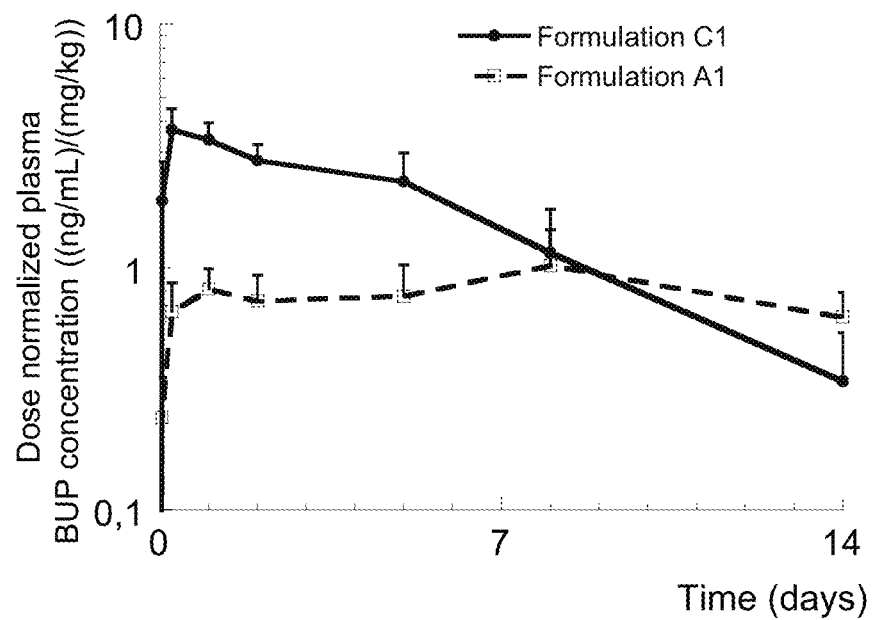

INJECTABLE BUPRENORPHINE FORMULATION

CROSS-REFERENCE TO RELATED PATENT APPLICATIONS

This application is a Divisional Application of U.S. application Ser. No. 15/520,946, filed Apr. 21, 2017; which is a national stage of PCT International Application No. PCT/EP2015/074901, filed Oct. 27, 2015; which claims priority to United Kingdom Application No. 1419091.2, filed Oct. 27, 2014, the contents of each of which are hereby incorporated by reference in their entirety.

FIELD

The present invention relates to injectable formulations of opioid agonists such as buprenorphine. In particular the invention relates to injectable lipid formulations having the ability to form controlled-release compositions upon injection.

BACKGROUND TO THE INVENTION

Many active pharmaceutical ingredients and other bioactive agents exhibit a functional concentration window in vivo such that blood plasma concentrations of active agent in particular range will provide the desired effect. Concentrations below the functional window are typically inactive or less effective and concentrations above the functional window have the potential to cause serious side-effects.

Opioid agonists are a prime example of pharmaceutical agents for which adherence to an effective functional window, which may vary significantly between patients and overtime, is of great importance. Opioids are indicated in many conditions including treatment of pain and in various forms for treatment and maintenance in opioid dependence. Insufficient dose, especially in subject accustomed to opioids, can cause debilitating and unpleasant withdrawal symptoms while excessive dose cause euphoria, reinforcement of dependence and ultimately potentially fatal respiratory depression.

A number of controlled release formulations which might potentially be applied to opioid agents have been proposed. Historically, most of these have relied on biodegradable polymers such as poly-lactate, poly-glycolate and copolymers of these moieties. More recently, some highly effective lipid-based depot formulations have been proposed, such as the diacyl glycerol and phospholipid formulations disclosed in WO2005/117830. Such lipid formulations are highly effective. However, there remains a need for simple alternative systems that can effectively deliver opioid active agents over extended periods. It would be an advantage if these could be provided with a smaller number of separate constituents and particularly if these were highly biocompatible and biotolerable.

The present inventors have now established that certain opioids, particularly buprenorphine and its salts and derivatives, can be delivered as a sustained-release injection in simple lipid vehicles, providing a high concentration of the active agent is used. Such formulations may be ineffective or inefficient at low concentrations of buprenorphine but provide a much more desirable release profile when the buprenorphine concentration is held above around 16% by weight.

SUMMARY OF THE INVENTION

In a first aspect, the present invention therefore provides an injectable liquid formulation comprising:

a) a lipid controlled-release matrix comprising at least 50% triacyl lipids;
b) at least one oxygen containing organic solvent;
c) at least 16% by weight of at least one active agent selected from buprenorphine and salts thereof, calculated as buprenorphine free base.

Preferred triacyl lipids in all aspects and embodiments of the present invention are triacyl glycerols (triglycerides).

Such injectable liquid formulations as described herein in all aspects and embodiments of the invention typically form a controlled-release composition upon administration to the body of a subject. Such a subject may be a human or animal subject such as any of those described herein.

The injectable liquid formulations described herein in all aspects and embodiments of the invention typically have at least one active agent selected from buprenorphine and salts thereof present at a level of greater than 21% (e.g. greater than 30%, such as 31 to 50%) by weight buprenorphine. Herein throughout, all percentages of buprenorphine are calculated by weight as percentage of buprenorphine free base in the complete formulation, unless otherwise stated.

The injectable liquid formulations of the invention may be administered to a suitable subject, particularly a mammalian subject in thereby form a controlled-release formulation. In a second aspect, the present invention therefore provides a controlled-release composition formed by administration to a (preferably human) subject of an injectable liquid formulation as described in any of the aspects or embodiments disclosed herein. Evidently, preferred formulations of the invention will result in preferred controlled-release compositions.

The controlled-release compositions of the invention show advantageous release profiles, particularly with regard to maintaining plasma concentrations of buprenorphine within a functional window for an extended period. Thus, following administration to said subject of an injectable liquid (as described in any embodiment herein) once monthly for at least 6 months, Cmin and Cmax (particularly the mean of each, taken in a population of subjects typically comprising at least at least 10 subjects) at a steady-state both fall with the range of between 0.2 ng/mL to 12 ng/mL, preferably 0.4 ng/mL and 15 ng/mL.

In a further aspect, the invention also provides a method of sustained delivery of buprenorphine to a human or non-human animal body, said method comprising administering an injectable liquid formulation comprising:

a) a lipid controlled-release matrix comprising at least 50% triacyl lipids;
b) at least one oxygen containing organic solvent;
c) at least 16% by weight of at least one active agent selected from buprenorphine and salts thereof, calculated as buprenorphine free base.

Such formulations and compositions of the present invention can be used in the treatment of any indication for which the chronic administration of buprenorphine is suitable. In a corresponding further aspect, the invention thus provides a method of treatment or prophylaxis of a human or non-human animal subject comprising administration of an injectable liquid formulation as described in any aspect or embodiment of the invention. Such a method may be for the treatment or prophylaxis of any suitable condition, including for the treatment of pain, for opioid maintenance therapy or for the treatment of opioid dependence by detoxification and/or maintenance or for the treatment or prophylaxis of the symptoms of opioid withdrawal and/or cocaine withdrawal.

Correspondingly, in a yet further aspect, the present invention provides an injectable liquid formulation or controlled-release composition as described herein for use in therapy. Such therapy may be for the treatment or prophylaxis of any suitable condition, including for the treatment of pain, for opioid maintenance therapy or for the treatment of opioid dependence by detoxification and/or maintenance or for the treatment or prophylaxis of the symptoms of opioid withdrawal and/or cocaine withdrawal.

DETAILED DESCRIPTION OF THE INVENTION

Highly effective lipid-based controlled-release formulations have been disclosed over the last few years, including formulations such as those of WO2005/117830 which comprise diacyl lipids and phospholipids in appropriate mixtures so as to generate formulations which change phase upon administration. This allows a low-viscosity formulation to be injected and to generate a higher viscosity depot composition in vivo which traps the active agent and provides a slow-release effect. Such compositions are effective for a broad range of active agents and rely primarily on the lipid matrix to control the active agent release.

The present inventors, during their work with lipid-based controlled-release formulations, have typically found that a lipid mixture and a phase-change upon injection as described above is generally necessary for controlled-release of most active agents. There are, however, certain bioactive agents that, depending on the therapeutic window (i.e. plasma concentration window where treatment effects are realized and side effects are acceptable), may be amenable to the use of simpler lipid formulations. The use of simpler systems is always an advantage in medicine because this reduces the number of components for which stringent sourcing and quality-control procedures must be established. Simpler systems also make the toxicological assessment and processes of regulatory approval less complex, particularly where the remaining excipients are generally regarded as safe (GRAS) or have an established record of pharmaceutical use, e.g., previous use in registered injection products.

It has now been established by the present inventors that certain opioid active agents, particularly buprenorphine and related compounds (salts and structural analogues thereof for example) can be released in a controlled fashion from triacyl-lipid containing formulations providing that the concentration of buprenorphine compound ("buprenorphine" being used herein to include all appropriate salts and structural analogues where context allows) is above a certain threshold level.

The need for buprenorphine to be at a high concentration is in itself unexpected because drug release in controlled-release formulations is generally controlled by the carrier matrix. The active agent will have the active role in the biological effect but typically exhibits a passive role in the controlled-release. Moreover, high concentrations of active agent will generally interfere with the function of the controlled-release matrix and thus the concentration of active agent will often be limited by the disruptive effect that such an agent has upon the controlled-release.

The present case is quite the reverse of the established norm and formulations having at least 16% buprenorphine are found to provide more effective release than similar formulations with a lower active-agent content.

The invention provides an injectable liquid formulation comprising:

a) a lipid controlled-release matrix comprising at least 50% triacyl lipids;
b) at least one oxygen containing organic solvent;
c) at least 16% by weight of at least one active agent selected from buprenorphine and salts thereof, calculated as buprenorphine free base.

In view of the positive effect that the buprenorphine component has upon the controlled-release behaviour of this system, the active agent (generally selected from buprenorphine, its structural analogues and salts thereof) is present at a level of greater than 16% in all aspects and embodiments of the invention. This will preferably be greater than 21% (e.g. greater than 30%, such as 31 to 50%) by weight buprenorphine (all calculated as buprenorphine free base). Concentrations of up to 60% buprenorphine may be used but preferably up to 50%, e.g. up to 45% will be used.

The advantage of high buprenorphine concentrations is illustrated in the attached FIG. 1. The Figure shows dose normalized plasma concentrations of buprenorphine after administration of a 33.8% formulation (A1) and a 1.06% formulation (C1) to rats. It is evident from FIG. 1 that formulation A1 provides a much more sustained and stable release of buprenorphine into blood plasma and has the potential to provide a much greater duration of release, since the level does not change significantly over the 14 day period of the experiment.

Another critical component in the liquid formulations and controlled-release compositions of the invention is the lipid matrix component a). In the injectable liquid formulations of all embodiments of the invention, component a) typically forms 10% to 70% of the total precursor formulation. This may be 15% to 64% or 20 to 50% by weight.

In lipid component a), at least 50% of the lipids are formed of triacyl lipids. Thus, generally 50% to 100% (such as at least 80%), preferably 60 to 90% or 60% to 95%, more preferably 70 to 90% of said lipid controlled release matrix (component b)) is formed of triacyl lipids. Component a) may consist essentially of triacyl lipids (e.g. be 95% or more triacyl lipids).

The triacyl lipids forming part or all of component a) may be any suitable triacyl lipid and will generally have a polar "head" group and three non-polar "tail" groups. Typically these will be joined by an ester moiety, although carbon-carbon bonds, ethers, amides etc. may be used. Suitable polar head groups (for the triacyl component and for any other lipids present) will generally be non-ionic and include polyols such as glycerol, diglycerol (and oligo/ploy glycerol such as 2 to 10 glycerols) and sugar or carbohydrate moieties (such as mono-, di-, and tri-saccharides including sorbitan, sorbitol, trehalose, inositol, glucose, maltose and sucrose moieties and derivatives thereof) and esters of polyols, such as acetate or succinate esters. Preferred polar groups are glycerol and diglycerol, especially glycerol.

Suitable non-polar "tail" groups (for the triacyl component and for any other lipids present) are typically C8 to C20 acyl groups which may have one or more unsaturations in the carbon chain. In one preferred embodiment, component a) may comprise lipids (particularly triacyl lipids) with "medium chain" fatty acyl components, such as C8 to C12 acyl chains (especially with zero, one or two unsaturations). Such components may comprise some or all of the triacyl lipid component, such as 1 to 100% of the triacyl lipid component (e.g. 1 to 70% or 10 to 50%). Preferably such components will comprise less than 50% of the triacyl lipids. In another and more preferred embodiment, the triacyl lipid and any other lipids present will comprise fatty acyl chains having 12 to 22 carbons, particularly C16 to C20 fatty acyl chains, especially with zero, one or two unsaturations.

In one embodiment, in the injectable liquid formulation of any aspect of the invention, component a) comprises at least 50% by weight of triacyl lipids with such triacyl lipids comprising C16 to C20 acyl groups having zero, one or two unsaturations. Among these, especially preferred groups include C16:0, C16:1, C18:0, C18:1, C18:2, C18:3 and/or C20:1 acyl groups.

In a further embodiment, the triacyl lipids of component a) of the present invention will comprise not more than 25% of acyl groups shorter than C12. That is to say, at least 75% of the acyl groups of the triacyl components will be C12 or longer (typically having zero, one or two unsaturations or a mixture thereof). This may be at least 85% acyl groups of C12 or longer or at least 90% acyl groups of C12 or longer.

In a further embodiment, the triacyl lipids of component a) may comprise acyl groups wherein at least 25% of such acyl groups are unsaturated (e.g. having 1, 2 or 3 unsaturations, preferably 1 or 2 unsaturations in the acyl chain). This will preferably be at least 50% (e.g. 50 to 100% or 50 to 95%) unsaturated acyl moieties and more preferably at least 75% unsaturated moieties in the triacyl component (e.g. triacyl glycerol or others described herein). In a similar embodiment, at least 50% by weight of triacyl lipids in component a) may comprise at least 1 unsaturated acyl moiety (e.g. at least one acyl moiety having 12 or more carbons in the acyl chain and 1 or 2 unsaturations in that chain).

Some examples of non-polar groups suitable for use in various embodiments of the present invention include caproyl (C6:0), capryloyl (C8:0), capryl (C10:0), lauroyl (C12:0), myristoyl (C14:0), palmitoyl (C16:0), phytanoly (C16:0), palmitoleoyl (C16:1), stearoyl (C18:0), oleoyl (C18:1), elaidoyl (C18:1), ricinoleoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, ricinoleic, linoleic, linolenic, arachidonic, behenic or lignoceric acids, or the corresponding alcohols. Preferable non-polar chains include palmitic, stearic, ricinoleic, oleic and linoleic acids, particularly oleic acid.

In a further preferred embodiment, the injectable liquid formulation of any aspect of the present invention may comprise at least 60% of triacyl lipids having C16 to C18 acyl groups with zero, one or two unsaturations. That is to say, of the triacyl lipids present, at least 60% of the non-polar groups will be C16 to C18, preferably, with zero, one or two unsaturations. The total triacyl lipid (e.g. triacyl glycerol) component present will be as indicated in any embodiment herein.

Triacyl lipids, such as triacyl glycerols, may be synthetic but will typically be derived from natural sources. Many oils of natural products are high in triacyl lipids and these may be used either in their extracted form or in partially or fully purified forms. Animal or preferably vegetable oils are highly suitable sources of triacyl lipids (especially triacyl glycerols) and may include olive oil, corn oil, sunflower oil, rapeseed (canola) oil, palm oil, soybean oil, sesame oil, castor oil and mixtures thereof. Sesame oil, soybean oil, castor oil and mixtures thereof are preferred.

In one embodiment, the lipid matrix component a) contains up to 50% of lipids that are not triacyl lipids. Such lipids may be any appropriate component including mono-, and di-glycerides, phospholipids (diacyl and/or "lyso" monoacyl), cholesterol, tocopherol etc. One preferred embodiment provides for the non-triacyl lipid to comprise:

i) at least one neutral diacyl lipid
ii) at least one tocopherol; and/or
iii) at least one phospholipid;

Lipids that are not triacyl lipids will evidently comprise that part of component a) which is not accounted for by triacyl lipids, thus, the amount on non-triacyl lipids may be, for example 0 to 49%, such as 1 to 40% or 3 to 30%. In one embodiment less than 10% of component a) (e.g. 0.5 to 10%) is a non-triacyl lipid, such as i) to iii) above or mixtures thereof.

Component i) above may be any neutral diacyl lipid and will typically comprise a non-ionic polar "head" group as described above, linked (e.g. by and ester, ether, C—C bond or amide) to two non-polar "tail" groups such as the acyl groups described herein. Preferred polar head groups and non-polar tail groups described herein above apply to the diacyl lipid component (and equally to any mono-acyl lipid that may be present).

Component ii) above is "tocopherols", which are a class of compounds which may be used as part of component a) in any compatible aspect or embodiment herein. As used herein, the term "a tocopherol" is used to indicate the non-ionic lipid tocopherol, often known as vitamin E, and/or any suitable salts and/or structural analogues thereof. Suitable analogues will be those providing the physical properties, lack of toxicity, and structure which is equivalent or highly similar to tocopherol itself. Such analogues will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous physical properties or lack of toxicity. Typically, a tocopherol will contain no more than 10% of non-tocopherol-analogue compounds, preferably no more than 5% and most preferably no more than 2% by weight.

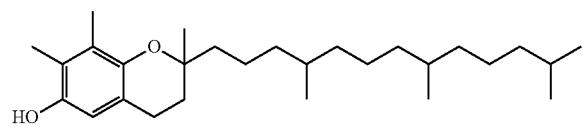

Tocopherol (Vitamin E)

Component iii) above is at least one phospholipid. As with triacyl and diacyl lipids, this component comprises a polar head group non-polar tail group(s). The key feature of the phospholipid lies principally in the polar group. The non-polar portions may thus suitably be derived from the fatty acids or corresponding alcohols considered above for triacyl lipids (e.g. independently chosen from C16 to C22 acyl groups with zero to two unsaturations). It will typically be the case that the phospholipid will contain two non-polar groups, although one or more constituents of this component may have one non-polar moiety. Where more than one non-polar group is present these may be the same or different.

Preferred phospholipid polar "head" groups include phosphatidylcholine, phosphatidylethanolamine, phosphatidylserine and phosphatidylinositol. Preferred phospholipids are phosphatidylcholine (PC), phosphatidylethanolamine (PE). Most preferred is phosphatidylcholine (PC).

The phospholipid portion, as well as the triacyl lipid and any diacyl lipid portion, may be derived from a natural source. Suitable sources of phospholipids include egg, heart (e.g. bovine), brain, liver (e.g. bovine) and plant sources including soybean, castor bean and sesame seed. Such sources may provide one or more constituents of component iii), which may comprise any mixture of phospholipids.

If one or more phospholipids are present in the injectable formulation of the invention then it is preferred that the ratio of triacyl lipid(s):phospholipid(s) (w/w) in the lipid controlled-release matrix a) is in the range of 50:50 to 100:0, preferably 80:20 to 100:0, especially 90:10 to 100:0, such as 93:7 to 100:0, 95:5 to 100:0 or 97:3 to 100:0.

Taken as a whole, the combined amount of phospholipid (s) present in the injectable formulation may be less than 8 wt % of the formulation, 6 wt % or less, 4 wt % or less, or 2 wt % or less. In particular, the amount of phospholipid in the formulation may be less than 5% by weight, such as less than 4.5% by weight (e.g. 0% to 4.4%), or less than 4.2% by weight of the total formulation (e.g. of the total of components a) to c)).

In a further embodiment, the amount of triacyl lipid in component a) of the formulation may be at least 90% by weight. This may be at least 95% (e.g. 96 to 100%) or at least 95.5%. Preferred triacyl lipids include those described herein, including triacylglycerols and triacyldiglycerols. In a corresponding embodiment, the amount of phospholipid in component a) may be less than 5% by weight, such as less than 4.5% by weight (e.g. 0 to 4.4% by weight), or less than 4.2% by weight of component a). Evidently, components b) and c) will generally not contain any phospholipid components.

Since the formulations of the invention are to be administered to a subject for the controlled release of an active agent, it is preferable that the components a and b, including components i) to iii) if present, are biocompatible. In this regard, it is preferable to use, for example, diacyl phospholipids rather than mono-acyl (lyso) compounds. A notable exception to this is tocopherol, as described above. Although having only one alkyl chain, this is not a "lyso" lipid in the convention sense. The nature of tocopherol as a well tolerated essential vitamin evidently makes it highly biocompatible.

In one embodiment, the formulations of the present invention comprise only a single extract or component as component a). That is to say, component a) may be a single naturally occurring mixture or a single mixture separated from a single natural product. Thus, component a) may consist of or consist essentially of a single vegetable oil. Suitable examples include castor oil or sesame oil. In such an embodiment, the compositions are comparatively simple to prepare and validate for tasks such as quality control and regulatory approval. This potentially makes them simpler and/or more economical to manufacture than comparable compositions containing mixtures of lipid components.

Component b) of the various aspects of the present invention is at least one oxygen-containing organic solvent. Organic solvents comprise at least one carbon and generally at least one carbon-hydrogen bond and in the case of component b) will contain at least one oxygen in their structure. Such solvents may also contain at least one other "heteroatom" such as nitrogen, sulphur or a halide (chloride, fluoride, bromide, iodide). It is preferred that component b) consists of at least 80% by weight solvents not containing any halogen, more preferably at least 95%. Conversely, it is preferred that component b) comprises at least 50% solvents having at least one nitrogen and/or sulphur atom in their structure. Preferred component b) will comprise at least 75% and preferably at least 90% of such solvents.

Preferred solvents will typically be around 45 to 500 g/mol in molar mass, more typically around 50 to 200 g/mol. Preferred solvents include alcohols, amides, including lactams, and sulphoxides. Thus, in one embodiment, component b) may comprise, consist essentially of, or consist of amides, sulphoxides or mixtures thereof.

Two highly preferred solvents which may be included (individually or as a mixture) in component b) are N-methyl-2-pyrrolidone (NMP) and dimethyl sulfoxide (DMSO). In one preferred embodiment applicable to any aspect or compatible embodiment of the invention, component b) will comprise at least 50% of NMP and/or DMSO. Preferably component b) will comprise at least 70% of NMP, DMSO or mixtures thereof, more preferably at least 80% and most preferably at least 90%. In one embodiment component b) consists of NMP, DMSO or mixtures thereof or consists essentially of such components.

As used herein, as with common use, the term "substantially" is used to indicate that an aspect or component is, in substance, defined by the indicated limitation but allows for insubstantial variation not having any material effect upon the nature or behaviour. Such variation might be by, for example 10% or preferably 5% from the indicated amount, state or behaviour. Similarly, a component that "consists essentially of" some stated component will, in essence, consist of that component but may contain small, trivial or unavoidable other components such as deliberate additives (e.g. flavourings, preservatives, tracers etc) or components that are not easily or economically separable (such as lipids with a distribution of chain lengths etc) including contaminants and/or impurities which do not change the essential behaviour of the stated component. A component "consisting essentially" of a stated compound or mixture may include such compound(s) in any amount that controls the essential behaviour but typically at greater than 90% (e.g. 90% to 100%), more preferably greater than 95% and most preferably greater than 98%. Terms "about" and "around" carry meanings equivalent to "substantially" or "essentially".

Component b) may be present at any amount that provides a formulation suitable for injection (e.g. subcutaneous injection). Such a formulation will have the sterility, biocompatibility etc. required of an injectable formulation but will additionally have a viscosity suitable for injection. Such viscosities are discussed herein and the solvent may be chosen and used at a level to provide any such viscosities. The solvent will also be required in order to help dissolve the active agent and provide suitable controlled release. Such properties may be optimised from the Examples and discussion herein.

Typically, the formulations of the present invention in all aspects will comprise component b) present at 10 to 60%, especially 15 to 50% by weight of the precursor formulation. This will preferably be 20 to 45%, most preferably 25 to 40% by weight.

Component c) of the formulations and compositions of all aspects and embodiments of the present invention is at least one active agent selected from buprenorphine and salts thereof, calculated as buprenorphine free base. This may be any suitably active and biotolerable form of any buprenorphine compound having an effect (e.g. agonism and/or antagonism) at one or more opioid receptors. Buprenorphine free base is the most preferred buprenorphine active agent and where weight percentages are specified herein, these are in terms of the equivalent amount of buprenorphine free base unless otherwise specified. Suitable salts, including mixtures thereof, may be used and these salts may be any biocompatible salt. Suitable salts include acetate, citrate, pamoate or halide (e.g. chloride or bromide) salts, or any of the many biocompatible salts which are known in the art. The structure of buprenorphine free base is shown below:

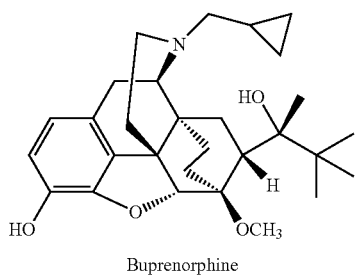 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

Buprenorphine

Buprenorphine is an opioid with mixed agonist-antagonist properties (also known as a partial agonist) that has been used in the treatment of opioid dependence in a number of countries. It is approved by the Food and Drug Administration (FDA) for the treatment of opioid dependence in the United States and clinical studies have shown buprenorphine to be effective in reducing opioid-positive urines and retaining patients in outpatient maintenance treatment of opioid dependence, as well as in the detoxification of opioid abusers.

Buprenorphine has a unique pharmacological profile with several potential strengths over other opioid treatments:
1. A ceiling on its agonist activity that may reduce its abuse liability and contribute to a superior safety profile.
2. Attenuation of physiological and subjective effects which likely contributes to the suppression of opioid self-administration.
3. Slow receptor dissociation providing extended duration.

Importantly, buprenorphine treatment is associated with a relatively low-intensity withdrawal syndrome upon discontinuation, making it particularly promising for detoxification treatments.

Buprenorphine is currently available commercially in sublingual dosing forms, which require dosing every 1-2 days either at a clinic, or with "take-home" medication. Because of the potential for abuse of opioids, however, "take-home" of any opioid poses potential logistic and legislative problems. This is made more problematic by the low bioavailability of existing sublingual formulations meaning that the dose being "taken home" is potentially quite a significant one.

A controlled-release formulation of the present invention offers several advantages in use for treating opioid dependence, including fast onset and relatively stable levels of buprenorphine over time, thereby suppressing withdrawal symptoms and blocking the effects of exogenously-administered opioids for several weeks. The slow decay and elimination of the depot buprenorphine could also provide a gradual opioid detoxification with minimal withdrawal syndrome. Hence, a controlled-release buprenorphine injection may offer a promising approach for delivering effective opioid maintenance or detoxification treatment. Furthermore, a controlled-release formulation administrable at intervals of at least 1 month should minimize the burdens of patient compliance as it would require a less frequent dosing regimen, thereby also reducing the frequency of clinic visits and the amount of clinical support needed. Finally, a periodic buprenorphine injection in controlled-release form should reduce the risks of misuse and drug diversion of the medication by eliminating or reducing the need for take-home medication.

The amount of buprenorphine required in the treatment of any particular subject will depend greatly upon the indication and upon the tolerance of the specific subject, as well as the frequency of administration and the rate of release following administration. In general, pain treatment will require lower doses than opioid dependence related therapies.

Buprenorphine will be present in the formulations of the present invention at 16% by weight or more as discussed herein.

The injectable liquid formulations in any aspects and embodiments of the present invention will generally have a dose of buprenorphine in the range 20 to 240 mg buprenorphine (calculated as free base) per month of release duration. The term "release duration" as used herein will be the period (typically the average or recommended period) between injections for a fully compliant subject. Suitable periods are discussed herein below. The buprenorphine content will thus depend upon the frequency of administration and may be, for example, 20 to 200 mg per month, preferably 20 to 1140 mg per month of buprenorphine (based upon equivalent amount of free base).

The total dose of buprenorphine or buprenorphine salt present will, as discussed above, depend upon the rate of release and frequency of administration. Typically, formulations in any aspect or embodiment of the present invention will have a dose in the range 20 to 800 mg, such as 50 to 600 mg buprenorphine per dose (calculated as free base) particularly 60 to 300 mg, more preferably 90 to 200 mg.

In all aspects and embodiments of the present invention, administration takes place on a periodic basis. Such administration will be less frequent than the dosing every 1-2 days used with current sublingual products. Generally the administration will be no more frequently than once every 28 days. An administration about once every 1 to 4 months may be desirable, such as every 28 to 136 or 28 to 96 days. This may be at periods of around 1 month, around 2 months or around 3 months. Thus, administration may be once every 28 to 32 days, once every 56 to 62 days, or once every 82 to 95 days. Such periods may be the recommended periods for administration and may be the periods between administration (generally the average periods) for a fully compliant subject.

The formulations in all aspects and embodiments of the invention are "injectable". Such formulations thus have the properties of sterility and biocompatibility required of a formulation for injection. Administration by injection is used herein to indicate any method in which the formulation is passed through the skin or other body surface, such as by needle, catheter or needle-less injector. Subcutaneous, intracavitary, intravitreal or intramuscular injection by any suitable method will thus be appropriate with subcutaneous or intramuscular, particularly subcutaneous injection being preferred.

Furthermore, such formulations must be capable of injection, preferably manually using convention equipment such as a disposable syringe and hypodermic needle of conventional gauge (e.g. 18 to 28 gauge). This requires that the formulations be of low viscosity. In all aspects of the present invention, the formulations are preferably low viscosity mixtures. Herein, the term "low viscosity mixture" is used to indicate a mixture which may be readily administered to a subject. This may be indicated, for example, by the ability to be dispensed from a 1 ml disposable syringe through a 22 gauge needle by manual pressure, preferably within a period of less than 1 minute. In a particularly preferred embodiment, the low viscosity mixture should be a mixture capable of passing through a standard sterile filtration membrane such as a 0.22 μm syringe filter. A typical range of suitable viscosities would be, for example, 20 to 600 mPas at 20° C., preferably 50 to 400 mPas at 20° C., most preferably 80 to 300 mPas at 20° C.

In addition to being a simple and highly effective controlled-release formulation, the formulations of the present invention are advantageous in that they may be provided in a form that does not require mixing or lengthy preparation before administration. Thus, in one embodiment, the formulations of the invention may be in ready-to-administer form. Such a form may be in a sealed vial or similar vessel, or in a pre-filled administration device, such as a pre-filled syringe or cartridge. Generally such a device will contain a single dose and optionally the means to vary the administered dose according to the needs of the subject (such as volume markings). Such pre-filled devices evidently form a further aspect of the invention.

The injectable formulations of the invention can be provided in ready-to-administer for because, in one embodiment, they can be stable to storage in such ready-to-administer form. Stability to storage will typically mean that a formulation of the invention will lose less than 20%, preferably less than 10%, more preferably less than 5% of its buprenorphine content after storage for at least 1 month, preferably at least 6 months, more preferably at least 12 months. Such storage will preferably be at 2-8° C., more preferably at 25° C.

When administered to a subject, the formulations of the present invention will preferably form the controlled-release compositions of the invention. This is typically upon contact with body fluid. Such subjects will be animal subjects, typically mammalian and most preferably human subjects.

It has been surprisingly established that in spite of the simplicity of the formulations of the present invention and the lack of essential need for a change of phase upon administration, the controlled-release compositions of the invention release buprenorphine in a very controlled fashion, providing that at least 16% of buprenorphine is present. Illustration of this is provided in FIG. 1 below.

Following administration to a subject of an injectable liquid formulation (as described in any appropriate embodiment herein) once monthly for at least 6 months, the average (mean) Cmin and Cmax (preferably in a population of at least 10 subjects) at a steady-state both fall with the range of between 0.3 ng/mL to 12 ng/mL, preferably 0.4 ng/mL and 5 ng/mL. This allows for the therapeutic window of buprenorphine to be maintained very effectively and gives a significantly improved experience for the subject.

The formulations of the invention will lose solvent component b) upon administration and my take up at least a little water. Such compositions after injection may thus comprise:
a) a lipid controlled-release matrix comprising at least 50% triacyl lipids;
b) optionally at least oxygen containing organic solvent;
c) at least 16% by weight of at least one active agent selected from buprenorphine and salts thereof, calculated as buprenorphine free base;
d) optionally at least one aqueous fluid.

Evidently, all of components a) to c) will correspond to any of those described herein for any aspect or embodiment of the invention. Aqueous component d), where present, will typically be an aqueous body fluid.

All of the injectable formulations described herein may be used in therapy. Such therapy will be for any condition for which buprenorphine is indicated, particularly over an extended period. Such indications include pain, particularly chronic pain including post-operative pain, cancer pain, and pain due to degenerative diseases such as arthritis. Most importantly, such indications will include treatment or maintenance in opioid dependence or withdrawal. Therapy for opioid dependence typically includes several phases of treatment including "induction", "stabilisation" and "maintenance". Formulations of the present invention may be used in any such phase, and/or in gradual dose reduction if desirable. Due to the long duration of the controlled-release effect, the formulations and compositions of the invention are very suitable for the maintenance phase. Thus, a subject who is receiving frequent injections (e.g. daily injections) or sublingual buprenorphine for opioid dependence may transition onto formulations of the present invention for stabilisation and/or maintenance phases of treatment.

In addition to use in opioid dependence, buprenorphine formulations of the present invention may be used in therapy relating to dependence on other substances including cocaine.

In view of the above, the present invention further provides methods of treatment of a human or animal subject (such as one described herein) comprising administering any of the formulations described herein. Such a method will typically be for the treatment of any conditions for which buprenorphine is indicated. These include all the conditions and therapies discussed herein in any aspect or embodiment of the invention.

The present invention will now be illustrated further by reference to the following non-limiting examples, and the attached figures.

BRIEF DESCRIPTION OF THE DRAWINGS:

FIG. 1. Shows dose normalized plasma buprenorphine (BUP) concentrations after subcutaneous administration of Formulations A1 and C1 (from Examples 1 and 3 respectively) to rats. The data points represent the mean value and error bars standard deviation (N=6).

EXAMPLES

Example 1. Composition Comprising Buprenorphine Base, Sesame Oil and N-Methyl Pyrrolidone (NMP)

The composition according to Table 1 was prepared by weighing 2.03 g buprenorphine base, 1.80 g NMP and 2.17 g of Sesame oil in a 10 mL injection glass vial. The vial was closed with Flurotec®-coated rubber stopper and aluminum crimp cap followed by end-over-end rotation mixing at ambient room temperature until a liquid, transparent and homogenous formulation was obtained. The formulation was finally subjected to filtration through a sterile 0.22 μm Millex®-GV membrane (Millipore) under nitrogen pressure.

TABLE 1

Composition of buprenorphine, triglyceride and solvent (wt %)

| Formulation | Buprenorphine | Sesame oil | NMP |
|---|---|---|---|
| A1 | 33.8 | 36.2 | 30.0 |

NMP = N-methyl pyrrolidone

Example 2. Compositions Comprising Buprenorphine Base, Triglycerides and Solvents The compositions according to Table 2 are prepared by weighing the required amounts of buprenorphine base, triglyceride and solvent in 4 mL injection glass vials. The vials are closed with Flurotec®-coated rubber stoppers and aluminum crimp caps followed by end-over-end rotation mixing at ambient room temperature.

TABLE 2

Composition of buprenorphine, triglyceride and solvent (wt %)

| Formulation | Buprenorphine | Sesame oil | Castor oil | MCT | NMP | DMSO |
|---|---|---|---|---|---|---|
| B1 | 33.8 | — | 36.2 | — | — | 30.0 |
| B2 | 25.4 | — | 44.6 | — | — | 30.0 |
| B3 | 16.9 | — | 63.1 | — | — | 20.0 |
| B4 | 40.0 | — | 20.0 | — | — | 40.0 |
| B5 | 25.4 | 44.6 | — | — | 30.0 | — |
| B6 | 16.9 | 63.1 | — | — | 20.0 | — |
| B7 | 40.0 | 20.0 | — | — | 40.0 | — |
| B8 | 33.8 | — | — | 36.2 | 30.0 | — |
| B9 | 25.4 | — | — | 44.6 | 30.0 | — |
| B10 | 16.9 | — | — | 63.1 | 20.0 | — |
| B11 | 40.0 | — | — | 20.0 | 40.0 | — |

DMSO = Dimethyl sulphoxide
NMP = N-methyl pyrrolidone
MCT = Medium Chain Triglycerides (e.g. Labrafac Lipophile WL 1349, Gattefossé, France)

Example 3. Composition Comprising Low Drug Load Buprenorphine Base, Triglyceride and Solvent The composition according to Table 3 was prepared by weighing 0.0424 g buprenorphine base, 0.400 g Ethanol and 3.558 g of Castor oil in a 10 mL injection glass vial. The vial was closed with Flurotec®-coated rubber stopper and aluminum crimp cap followed by end-over-end rotation mixing at ambient room temperature until a liquid, transparent and homogenous formulation was obtained. The formulation was finally subjected to filtration through a sterile 0.22 µm Millex-GP membrane (Millipore) under nitrogen pressure.

TABLE 3

Composition of buprenorphine, triglyceride and solvent (wt %)

| Formulation | Buprenorphine | Castor oil | EtOH |
|---|---|---|---|
| C1 | 1.06 | 88.94 | 10.00 |

EtOH = Ethanol

Example 4. Pharmacokinetics of Formulations Comprising Buprenorphine Base, Triglycerides and Solvents in Rat Formulations A1 (see Example 1) and C1 (see Example 3) were administered subcutaneously to rats in doses of 30 and 2 mg/kg, respectively (N=6 per group). Blood samples were collected up to 14 days after dosing. The plasma concentrations were determined as described below and the respective dose normalized pharmacokinetic profiles are shown in FIG. 1. As can be seen, Formulation A1 provides a rapid onset of buprenorphine release and stable buprenorphine plasma levels thereafter. In contrast, the plasma buprenorphine levels decline more rapidly after the initial peak for the low buprenorphine loading Formulation C1. In summary, Formulation A1 is seen to provide stable plasma levels over the entire study period whereas the buprenorphine levels for Formulation C1 decline about one order of magnitude during the same period.

Protocol:

Formulations A1 and C1 were administered subcutaneously to rats (male MPF Sprague-Dawley rats) in doses of 30 and 2 mg/kg, respectively, and blood samples were collected pre-dose, and at 1 hour, 6 hours, 1 day, 2 days, 5 days, 8 days, 14 days after dosing. A blood volume of 0.25 mL was collected into EDTA-treated test tubes (Capiject® 3T-MQK, Terumo Medical Corporation) by sub-lingual bleeding. The blood samples were placed on ice immediately after collection and centrifuged (approximately 1500×g, at 5° C. for 10 min) within 30 to 60 minutes. The plasma was transferred into 0.5 mL propylene test tubes (Eppendorf Safe lock tubes, Fisher Scientific) and stored below −70° C. until bioanalysis. The plasma concentrations were determined with the aid of a commercial ELISA kit adapted for analysis of buprenorphine in rat plasma.

The invention claimed is:

1. A method for the treatment of pain, for opioid maintenance therapy, or for the treatment of opioid dependence by detoxification and/or maintenance or for the treatment of the symptoms of opioid withdrawal and/or cocaine withdrawal, comprising the subcutaneous administration to a human or non-human animal subject in need thereof a therapeutically effective amount of an injectable liquid formulation comprising:
   a) a lipid controlled-release matrix comprising at least 80% triglycerides;
   b) at least one oxygen containing organic solvent; and
   c) 50-600 mg of at least one active agent selected from buprenorphine and salts thereof, calculated as buprenorphine free base,
wherein the injectable liquid formulation is administered to the subject every 2 or 3 months,
wherein the injectable liquid formulation comprises at least 16% by weight of the active agent.

2. The method of claim 1, wherein component a) comprises at least 90% triglycerides.

3. The method of claim 1, wherein component a) comprises at least 95% triglycerides.

4. The method of claim 1, wherein component a) further comprises:
   i) at least one neutral diacyl lipid
   ii) at least one tocopherol; and/or
   iii) at least one phospholipid.

5. The method of claim 1, wherein component a) comprises 10 to 60 wt. % of the total injectable liquid formulation.

6. The method of claim 1, wherein component a) comprises at least 50 wt. % of triglycerides comprising C16 to C20 acyl groups having zero, one, or two unsaturations.

7. The method of claim 1, wherein component a) comprises at least 60 wt. % of triglycerides comprising C16 to C18 acyl groups with zero, one, or two unsaturations.

8. The method of claim 1, wherein component b) is present at 15 to 50 wt. % of the total injectable liquid formulation.

9. The method of claim 1, wherein component b) comprises at least one amide and/or at least one sulphoxide.

10. The method of claim 9, wherein component b) comprises N-methyl-2-pyrrolidone (NMP), dimethyl sulfoxide (DMSO), or mixtures thereof.

11. The method of claim 1, wherein the injectable liquid formulation is in ready-to-administer form.

12. The method of claim 1, wherein the injectable liquid formulation has a viscosity of 20 to 600 mPas at 20° C.

13. The method of claim 4, wherein the ratio of triglyceride(s):phospholipid(s) (w/w) in the lipid controlled-release matrix a) is in the range of 90:10 to 100:0.

14. The method of claim 4, wherein the level of phospholipid in the injectable liquid formulation as a whole is less than 8 wt. %.

15. The method of claim 1, wherein component a) comprises greater than 90% triglycerides, and wherein component a) comprises at least 50 wt. % of triglycerides comprising C16 to C20 acyl groups having zero, one, or two unsaturations.

16. The method of claim 1:
wherein component a) forms 10 to 70 wt. % of the total injectable liquid formulation,
wherein component b) is present at 10 to 60 wt. % of the total injectable liquid formulation,
wherein component b) comprises at least 50% N-methyl-2-pyrrolidone (NMP), dimethyl sulfoxide (DMSO), or mixtures thereof.

17. The method of claim 1:
wherein component a) forms 10 to 60 wt. % of the total injectable liquid formulation,
wherein component b) is present at 15 to 50 wt. % of the total injectable liquid formulation,
wherein component b) comprises at least 70% N-methyl-2-pyrrolidone (NMP), dimethyl sulfoxide (DMSO), or mixtures thereof.

18. The method of claim 1:
wherein component a) forms 15 to 64 wt. % of the total injectable liquid formulation,
wherein of component a) comprises at least 90% triglycerides,
wherein component b) is present at 20 to 45 wt. % of the injectable liquid formulation,
wherein component b) comprises at least 80% N-methyl-2-pyrrolidone (NMP), dimethyl sulfoxide (DMSO), or mixtures thereof.

19. The method of claim 1:
wherein component a) forms 20 to 50 wt. % of the total injectable liquid formulation,
wherein component a) comprises at least 95% triglycerides,
wherein component b) is present at 25 to 40 wt. % of the injectable liquid formulation,
wherein component b) comprises at least 90% N-methyl-2-pyrrolidone (NMP), dimethyl sulfoxide (DMSO), or mixtures thereof.

20. The method of claim 19, wherein component b) is NMP.

21. The method of claim 1, wherein the injectable liquid formulation comprises 50-600 mg of the at least one active agent per dose.

22. The method of claim 1, wherein the injectable liquid formulation comprises a single dose of 50-600 mg of the at least one active agent.

* * * * *